US010416035B2

(12) United States Patent
Rubinstein et al.

(10) Patent No.: US 10,416,035 B2
(45) Date of Patent: Sep. 17, 2019

(54) POWER MANAGEMENT SYSTEM FOR PRESSURE MONITORING

(71) Applicant: MIJA Industries, Inc., Rockland, MA (US)

(72) Inventors: Jorge Rubinstein, Newton, MA (US); Robert M. Manning, Weymouth, MA (US); John J. McSheffrey, Hingham, MA (US)

(73) Assignee: MIJA INDUSTRIES, INC., Rockland, MA (US)

( * ) Notice: Subject to any disclaimer, the term of this patent is extended or adjusted under 35 U.S.C. 154(b) by 174 days.

(21) Appl. No.: 15/817,024

(22) Filed: Nov. 17, 2017

(65) Prior Publication Data

US 2018/0348075 A1 Dec. 6, 2018

Related U.S. Application Data

(60) Provisional application No. 62/512,217, filed on May 30, 2017.

(51) Int. Cl.
*G01L 19/00* (2006.01)
*H01H 47/02* (2006.01)
(Continued)

(52) U.S. Cl.
CPC ......... *G01L 19/00* (2013.01); *A61M 16/0051* (2013.01); *A61M 16/022* (2017.08);
(Continued)

(58) Field of Classification Search
CPC .... F17C 1/00; F17C 13/025; F17C 2221/011; F17C 2223/0123; F17C 2223/035;
(Continued)

(56) References Cited

U.S. PATENT DOCUMENTS 6,314,059 B1 * 11/2001 Shimizu ................... G04C 3/00
368/157
7,742,273 B1 * 6/2010 Shvartsman ....... H03K 17/0822
307/10.1
(Continued)

OTHER PUBLICATIONS

McDaniel, Wharton, A Simple Solution for Switching Multiple Power Sources in Notebook Computers, Apr. 13, 1998, pp. 1-6, Vishay Document No. 70786, AN810, www.vishay.com/docs/70786/70786.

*Primary Examiner* — Alfonso Perez Borroto
*Assistant Examiner* — Esayas G Yeshaw
(74) *Attorney, Agent, or Firm* — Douglas Denninger

(57) ABSTRACT

A power management system and method including a normally-open switch, an on/off circuit, a microprocessor, and at least one sensor to monitor a condition. The on/off circuit includes an on/off control gate-controlled switch device such as a PMOS device for system power, a flip/flop switch to respectively activate and deactivate the on/off control PMOS device, and a transition detection circuit connected to the normally-open switch. A single DC power source establishes a source voltage to power the on/off circuit and the normally-open switch. The transition detection circuit generates an "on" signal when the user initially activates the normally-open switch, and supplies the "on" signal to the flip/flop switch to change it to an "on" state to activate the on/off control PMOS device. While activated, the on/off control PMOS device enables system power from the power source to be provided to at least the sensor and the microprocessor. The microprocessor generates an "off" signal when the normally-open switch is activated for at least a selected period of time, and supplies the "off" signal to the flip/flop switch to change it to an "off" state to deactivate the on/off control PMOS device and thereby disable system power to at least the sensor and the microprocessor.

25 Claims, 13 Drawing Sheets

(51) Int. Cl.

| | |
|---|---|
| *H03K 17/687* | (2006.01) |
| *H02H 3/18* | (2006.01) |
| *G01L 7/04* | (2006.01) |
| *A61M 16/00* | (2006.01) |
| *F17C 1/00* | (2006.01) |
| *A61M 16/10* | (2006.01) |
| *H03K 17/10* | (2006.01) |
| *F17C 13/02* | (2006.01) |
| *G01L 19/08* | (2006.01) |

(52) U.S. Cl.
CPC ............ *A61M 16/1005* (2014.02); *F17C 1/00* (2013.01); *F17C 13/025* (2013.01); *G01L 7/04* (2013.01); *H01H 47/02* (2013.01); *H02H 3/18* (2013.01); *H03K 17/102* (2013.01); *H03K 17/6871* (2013.01); *A61M 2016/0027* (2013.01); *A61M 2202/0208* (2013.01); *A61M 2205/18* (2013.01); *A61M 2205/3331* (2013.01); *A61M 2205/581* (2013.01); *A61M 2205/583* (2013.01); *A61M 2205/584* (2013.01); *A61M 2205/8206* (2013.01); *F17C 2221/011* (2013.01); *F17C 2223/0123* (2013.01); *F17C 2223/035* (2013.01); *F17C 2250/036* (2013.01); *F17C 2250/043* (2013.01); *F17C 2250/0491* (2013.01); *F17C 2250/077* (2013.01); *F17C 2265/04* (2013.01); *F17C 2270/025* (2013.01); *G01L 19/083* (2013.01)

(58) Field of Classification Search
CPC ......... F17C 2250/036; A61M 16/0051; A61M 2202/0208; A61M 2205/3331; A61M 2205/583; A61M 2205/8206; A61M 16/1005; A61M 16/022; A61M 2016/0027; A61M 2205/581
See application file for complete search history.

(56) References Cited

U.S. PATENT DOCUMENTS

| | | | | |
|---|---|---|---|---|
| 8,174,961 | B2* | 5/2012 | Koo | H03K 17/0822 |
| | | | | 341/143 |
| 8,203,359 | B2* | 6/2012 | Dequina | H02M 3/156 |
| | | | | 323/265 |
| 9,306,493 | B2* | 4/2016 | Schatzberger | H03K 4/501 |
| 2003/0197426 | A1* | 10/2003 | Carson | H04B 3/54 |
| | | | | 307/40 |

* cited by examiner

POWER MANAGEMENT SYSTEM FOR PRESSURE MONITORING

CROSS-REFERENCE TO RELATED APPLICATION

This application claims the benefit of U.S. Provisional Patent Application No. 62/512,217 filed May 30, 2017 and U.S. Design patent application No. 29/585,168 filed 21 Nov. 2016. Each of the above-identified applications is incorporated herein by reference in its entirety.

FIELD OF THE INVENTION

This invention relates to electronic power management systems and more particularly to systems which conserve battery power utilized by electronic circuits to monitor pressure in a tank, a cylinder or other fluid storage unit.

BACKGROUND OF THE INVENTION

There are a number of situations where it is desirable to monitor automatically one or more parameters. It is also desirable to enhance mobility and portability by efficiently utilizing battery-powered circuits, such as in electronic monitoring systems. One common situation is monitoring medical oxygen being inhaled by patients. Research shows that a number of patients in medical facilities have had medical issues caused by low oxygen or by running out of oxygen completely. The most common method of oxygen monitoring is performed using an analog pressure gauge mounted to an oxygen regulator that requires a medical professional to visually monitor the pressure in the oxygen tank by actual visual inspection of the pressure gauge.

Other forms of oxygen monitoring are currently available, including electronic versions that will monitor oxygen with a digital display representing the pressure in the oxygen tank. Many of these devices also have alarms to notify the user when the oxygen level is at a low level. These devices typically are battery operated and have no monitoring ability should the power level of the batteries become too low.

The lack of a backup capability in the event of power loss was seen as a deficiency by the Applicant. It would be desirable to have a pressure monitoring system that would remain functioning even if the battery was unable to power the electronics.

SUMMARY OF THE INVENTION

An object of the present invention is to provide a power management system suitable for electronic circuits to monitor pressure in a tank, a cylinder or other storage unit.

Another object of the present invention is to obviate the need for a second power source while accomplishing power management.

A further object of the present invention is to combine an electronic pressure monitoring system with a mechanical device such as reed switch on an analog gauge which operates independently of system power.

Yet another object of the present invention is to decrease the overall size and costs for power management systems utilizing gate-controlled switching devices such as FET (field-effect transistor) devices, particularly P-channel enhancement FET, and more particularly PMOS (P-channel metal oxide semiconductor) devices.

This invention features a power management system for use with a single DC (direct or constant current) power source having inversion protection, the system including a normally-open switch that can be activated by a user, an on/off circuit, a microprocessor, and at least one sensor to monitor a condition. The on/off circuit includes an on/off control gate-controlled switching device, such as a PMOS device, for system power. In some embodiments, the on/off circuit further includes a flip/flop switch having an "on" state and an "off" state to respectively activate and deactivate the on/off control gate-controlled switching device, and a transition detection circuit connected to the normally-open switch. The microprocessor receives inputs from at least the normally-open switch and the sensor. The power source with inversion protection establishes a source voltage to power the on/off circuit and the normally-open switch. The transition detection circuit generates an "on" signal when the user initially activates the normally-open switch, and supplies the "on" signal to the flip/flop switch to change it to the "on" state to activate the on/off control gate-controlled switching device. While activated, the on/off control gate-controlled switching device enables system power from the power source to be provided to at least the sensor and the microprocessor. The microprocessor generates an "off" signal when the normally-open switch is depressed for at least a selected period of time, and supplies the "off" signal to the flip/flop switch to change it to the "off" state to deactivate the on/off control gate-controlled switching device and thereby disable system power to at least the sensor and the microprocessor.

In certain embodiments, the system further includes the inversion protection circuit with a second gate-controlled switching device to accomplish inversion protection, the on/off control gate-controlled switching device is a P-channel enhancement FET device and the inversion protection circuit gate-controlled switching device is a second P-channel enhancement FET device that is electrically separate from the on/off control P-channel enhancement FET device. In a number of embodiments, the on/off control gate-controlled switching device is a PMOS device and the inversion protection circuit gate-controlled switching device is a second PMOS device that is electrically separate from, but physically connected to, the on/off control PMOS device. In some embodiments, each PMOS device is configured as a three-terminal device, each with a source terminal, a drain terminal, and a gate terminal, and each PMOS device includes a parasitic internal diode located between the source and drain terminals of that device.

In some embodiments, the inversion protection PMOS device has its drain terminal connectable to a first terminal of the power source having a first polarity such as a positive polarity, its gate terminal is connected to a second terminal of the power source having a second polarity such as ground (zero) polarity, and its source terminal powers the on/off control PMOS device, the flip-flop switch and the transition detection circuit. The on/off control PMOS device has its source terminal connected to the source terminal of the inversion protection PMOS device, its gate terminal connected to the flip-flop switch output, and its drain terminal powers at least the sensor and the microprocessor.

In preferred embodiments, the circuit topology ensures a specific behavior of the parasitic internal diode in each one of the PMOS devices as follows. The parasitic internal diode of the inversion protection PMOS device creates an open circuit if the battery polarity is inverted thus avoiding the flow of potentially damaging inverted current. In one embodiment, the parasitic internal diode of the on/off control PMOS device creates an open circuit if the flip-flop switch output applies a positive voltage on the gate terminal of the on/off control PMOS device that forces the on/off control PMOS to turn off. This avoids any potential flow of supply current, effectively shutting off power at least to the sensor and microprocessor.

In certain embodiments, the inversion protection PMOS device and the on/off control PMOS device are formed on a single integrated circuit package as electrically separate devices. In some embodiments, the flip/flop switch and the transition detection circuit utilize different portions of a quad-NOR device. The normally-open switch includes a push-button switch that, when depressed by the user, sends a switch signal to the transition detection circuit and the microprocessor.

This invention further features a circuit utilizing a single power source to provide inversion protection and power management to a load, the circuit including first and second gate-controlled switching devices, each switching device having a source terminal, a drain terminal and a gate terminal, with a parasitic internal diode located between the source and drain terminals and having a cathode connected to the source terminal and an anode connected to the drain terminal. The first switching device has its drain terminal connectable to a first terminal of the power source having a first polarity, its gate terminal is connectable to a second terminal of the power source having a second polarity to provide inversion protection, and its source terminal powers at least the second switching device. The second switching device has its source terminal connected to the source terminal of the first switching device, its gate terminal connected to a control switch to provide on/off control, and its drain terminal powers the load. The parasitic internal diode of the second switching device has it cathode connected to its source terminal, with its anode connected to the load, and therefore is connected to conduct only toward the power source.

This invention also features a method for managing power from a DC power source having inversion protection, including selecting a normally-open switch such as a push-button that can be activated by a user, selecting an on/off circuit having an on/off control gate-controlled switching device such as a PMOS device for system power, a flip/flop switch having an "on" state and an "off" state to respectively activate and deactivate the on/off control PMOS device, and a transition detection circuit connected to the user switch, and selecting a microprocessor and at least one sensor to monitor a condition. The method further includes establishing a source voltage from the power source to power the on/off circuit and the user switch, and utilizing the transition detection circuit (1) to generate an "on" signal when the user initially activates the switch, such as by depressing it, and (2) to supply the "on" signal to the flip/flop switch to change the flip/flop switch to the "on" state to activate the on/off control PMOS device which, while activated, enables system power from the power source to be provided to at least the sensor and the microprocessor. The microprocessor is utilized (1) to generate an "off" signal when the normally-open switch is depressed or otherwise activated for at least a selected period of time and (2) to supply the "off" signal to the flip/flop switch to change it to the "off" state to deactivate the on/off control PMOS device and thereby disable system power to at least the sensor and the microprocessor.

Systems and methods according to the present invention are suitable for use in pressure monitoring systems such as one developed by the Applicant and referred to as a "Critical Alert Universal" system or "CAU" system. In some embodiments, power is managed in a pressure gauge monitoring system such as a CAU including a spiral Bourdon element, a socket, a housing, a dial, a main PCB with a mechanical push button switch to silence an alarm as well as to turn power on or off. The CAU is designed as a direct replacement, sometimes referred to as a "retrofit", for standard analog pressure gauges used on medical type regulators. The Critical Alert Universal combines electronics according to the present invention with an analog pressure gauge in one embodiment, and has three indicator lights on the face: battery (yellow), low pressure (red) and operating pressure (green). The Critical Alert Universal continually measures the pressure in the oxygen or compressed gas tank using an analog gauge. An audible alarm will sound along with a flashing red LED light when the oxygen or compressed gas gets to a preset low level. The user has the ability to silence the audible alarm by activating a "snooze" mode using a front mounted push-button-type switch that also acts as the power switch for the device.

The Critical Alert Universal allows for the medical professional to monitor the oxygen tank pressure from across the room, or even remotely via wireless interface, and does not require a person to move right up to the device to obtain an accurate reading as must be done for most conventional pressure monitoring devices. The audible alarm as well as the flashing red light alert the user that the oxygen pressure is at a low level and requires attention. The Critical Alert Universal also has a yellow indicator light for the battery which will flash when the battery voltage level drops to a programmed value. The advantage of using the analog gauge over a digital gauge is the user has an accurate way of monitoring the pressure level in the oxygen/compressed gas tank even with no power to the CAU device.

The Critical Alert Universal preferably utilizes electronic board mounted components to replace a mechanical on/off switch. The components allow a user to power up the device, silence an alarm and to power down. The electronic switch includes a dual PMOS, Quad 2-Input NOR Gate, resistor and capacitors. In one embodiment, the Critical Alert Universal will fit onto the majority of compressed gas regulators using a ⅛"-27 NPT fitting. This will allow use and added monitoring abilities to a multitude of facilities and applications.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

This invention may be accomplished by a power management system for use with a DC (direct or constant current) power source having inversion protection, the system including a normally-open switch such as a push-button or rocker-type switch that can be activated by a user, an on/off circuit, a microprocessor, and at least one sensor to monitor a condition. The on/off circuit includes an on/off control gate-controlled switching device for system power such as a PMOS device or other P-channel enhancement FET device. Also included in the on/off circuit is a flip/flop switch having an "on" state and an "off" state to respectively activate and deactivate the on/off control PMOS device, and a transition detection circuit connected to the normally-open switch. The microprocessor receives inputs from at least the normally-open switch and the sensor. The power source with inversion protection establishes a source voltage to power the on/off circuit and the normally-open switch.

The transition detection circuit generates an "on" signal when the user initially activates the normally-open switch, and supplies the "on" signal to the flip/flop switch to change it to the "on" state to activate the on/off control PMOS device. While activated, the on/off control PMOS device enables system power from the power source to be provided to at least the sensor and the microprocessor. The microprocessor generates an "off" signal when the normally-open switch is depressed for at least a selected period of time, and supplies the "off" signal to the flip/flop switch to change it to the "off" state to deactivate the on/off control PMOS device and thereby disable system power to at least the sensor and the microprocessor.

The present invention may also be accomplished by a circuit utilizing a single power source to provide inversion protection and power management to a load, the circuit including first and second gate-controlled switching devices, each switching device having a source terminal, a drain terminal and a gate terminal, with a parasitic internal diode located between the source and drain terminals. The first switching device has its drain terminal connectable to a first terminal of the power source having a first polarity, its gate terminal is connectable to a second terminal of the power source having a second polarity to provide inversion protection, and its source terminal powers at least the second switching device. The second switching device has its source terminal connected to the source terminal of the first switching device, its gate terminal connected to a control switch to provide on/off control, and its drain terminal powers the load. The parasitic internal diode of the second switching device has its cathode connected to its source terminal, with its anode connected to the load, and therefore is connected to conduct current only toward the power source.

Figure 1:
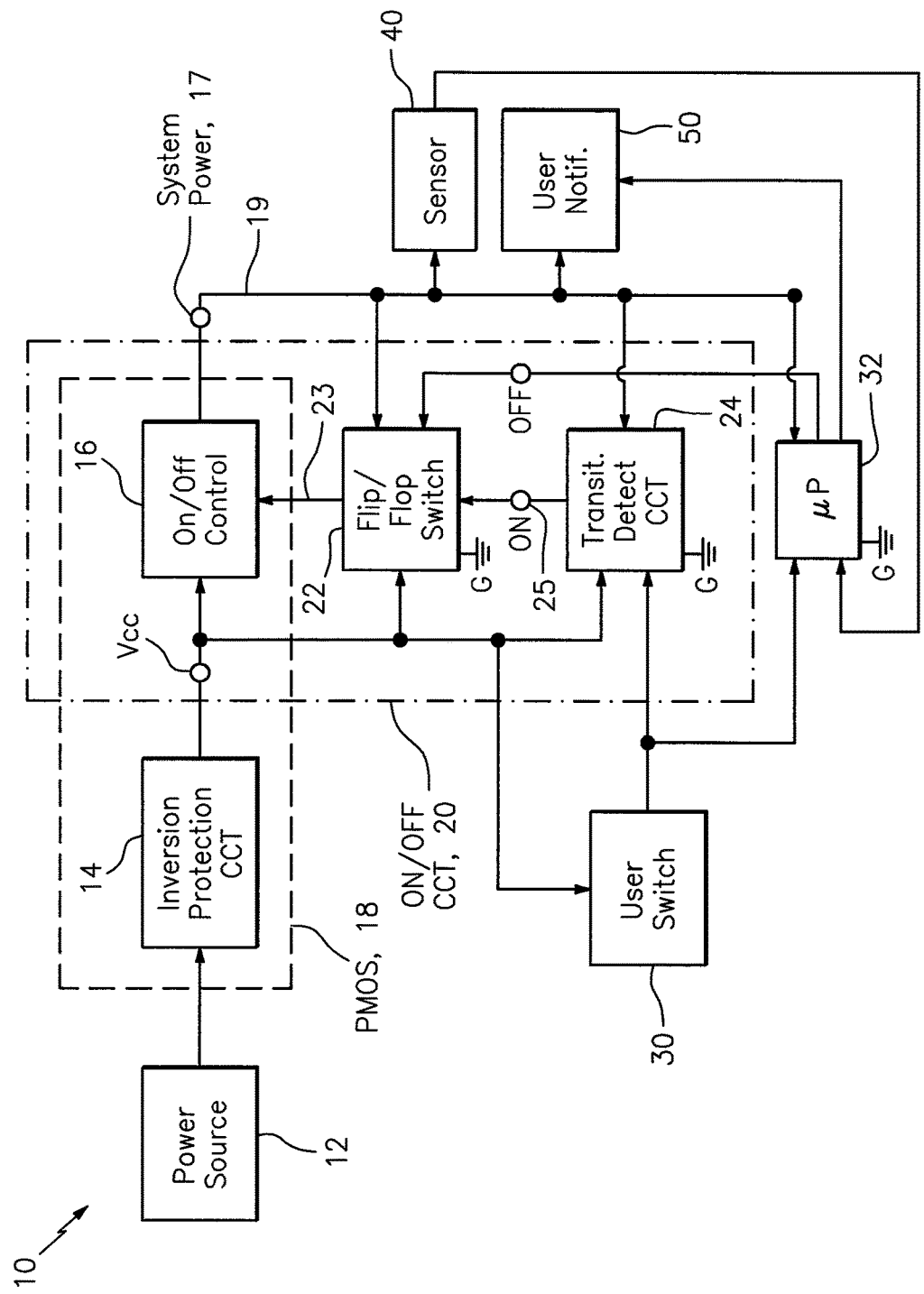
FIG. 1 is a schematic diagram of a power management system according to the present invention.

In one construction, power management system 10, FIG. 1, includes inversion protection circuit 14 connectable to first and second terminals of a DC power source 12 such as a 3-Volt battery. System 10 includes a user switch 30 such as a push-button, a rocker-type switch, or other normally-open switch that can be activated by a user. The term "normally-open switch" is intended to include "push-to-make" switches and "single pole, single throw normally open" switches. System 10 further includes an on/off circuit 20, a microprocessor 32, and at least one sensor 40 to monitor a condition such as pressure in a storage unit. A user notification device 50 provides a perceptible message to the user such as an audible alarm, a visible light, text, and/or other indication of the condition being monitored. In certain constructions, a message is transmitted wirelessly or remotely (such as via the internet) to the user.

The on/off circuit 20 includes an on/off control PMOS device 16 for system power 17 within supply line 19, a flip/flop switch 22 having an "on" state and an "off" state to respectively activate and deactivate the on/off control PMOS device 16, and a transition detection circuit 24 connected to the user switch 30. As described in more detail below beginning with FIG. 7A, in certain constructions inversion protection circuit 14 and on/off control PMOS device 16 are implemented by a dual PMOS component 18 as indicated in phantom in FIG. 1.

The microprocessor 32 receives inputs from at least the user switch 30 (indirectly via a logic inversion in this construction) and the sensor 40. The power source 12 with inversion protection 14 establishes a power source voltage Vcc to power the on/off circuit 20 and the user switch 30. In this construction, source voltage Vcc is established for on/off control PMOS device 16, flip/flop switch 22 and transition detection circuit 24. At least the flip/flop switch 22, the transition detection circuit 24 and the microprocessor 32 are connected to ground G in this construction, as illustrated in FIG. 1.

The transition detection circuit 24 generates an "on" signal 25 when the user initially activates the switch 30, and supplies the "on" signal 25 to the flip/flop switch 22 to change it to the "on" state to activate the on/off control PMOS device 16 via line 23. While activated, the on/off control PMOS device 16 enables system power 17 from the power source 12 to be provided to at least the sensor 40 and the microprocessor 32. The microprocessor generates an "off" signal when the user switch is depressed for at least a selected period of time, and supplies the "off" signal to the flip/flop switch to change it to the "off" state to deactivate the on/off control PMOS device 16 and thereby disable system power to at least the sensor and the microprocessor.

Figure 2:
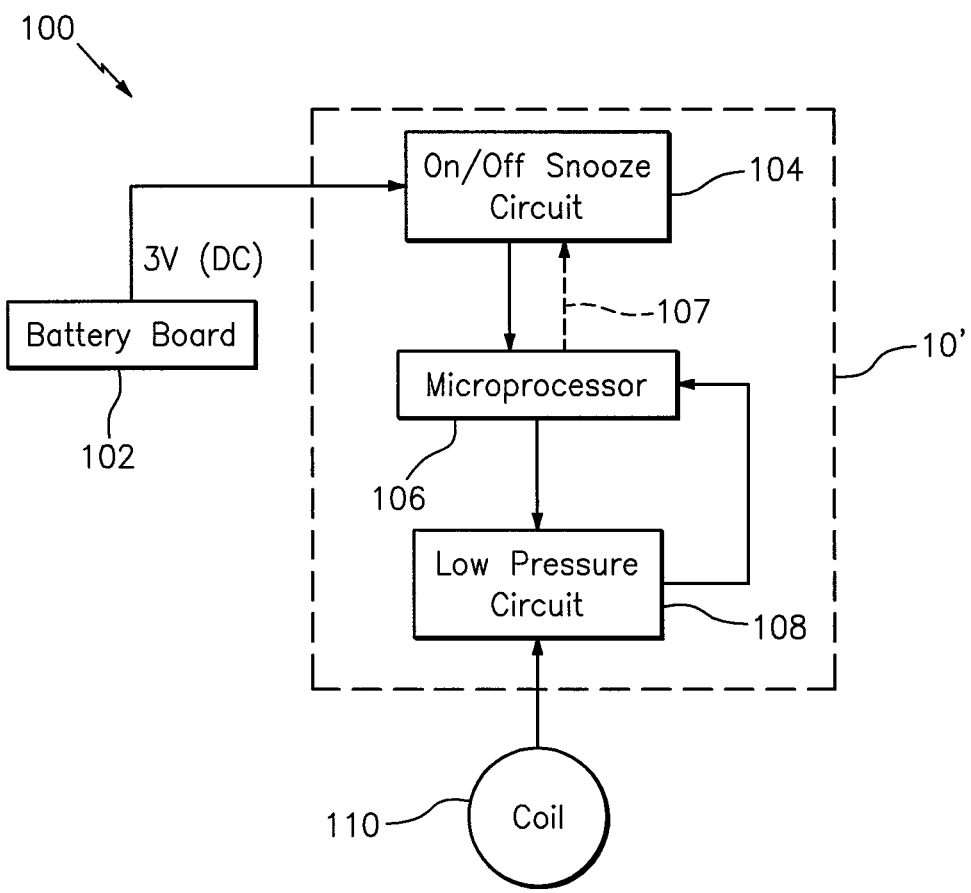
FIG. 2 is a schematic diagram of a power management system according to the present invention integrated with a pressure monitoring system.

In some implementations according to the present invention, a power management system 10', FIG. 2, is integrated into a pressure monitoring system 100. Power management system 10' includes on/off/snooze circuit 104, a microprocessor 106, and a low pressure detection circuit 108. In some constructions, as indicated by dashed arrow 107, microprocessor 106 controls certain functions of circuit 104 such as when the snooze feature is activated, and its duration. Pressure monitoring system 100 further includes a coil 110 such as a spiral Bourdon tube, and is connectable to a battery board 102 which supplies 3 Volts DC in one construction. Movement of the spiral Bourdon tube beyond a predetermined position activates a reed switch as described in more detail below.

Figure 3:
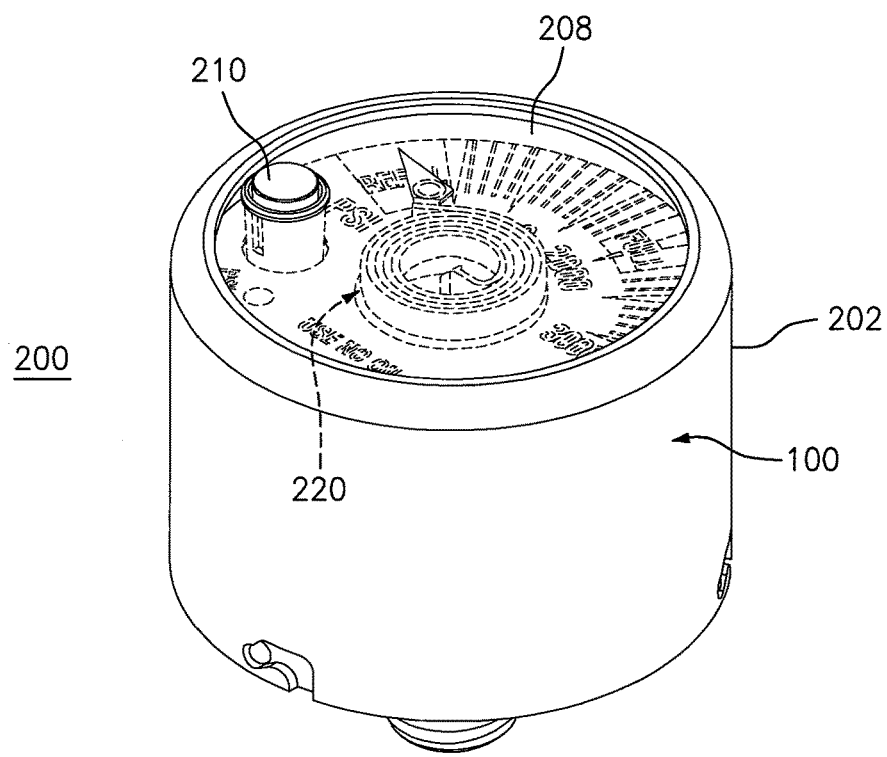
FIG. 3 is a perspective upper view of a PRESSURE GAUGE HOUSING that contains one embodiment of a pressure monitoring system according to the present invention.
Figure 4:
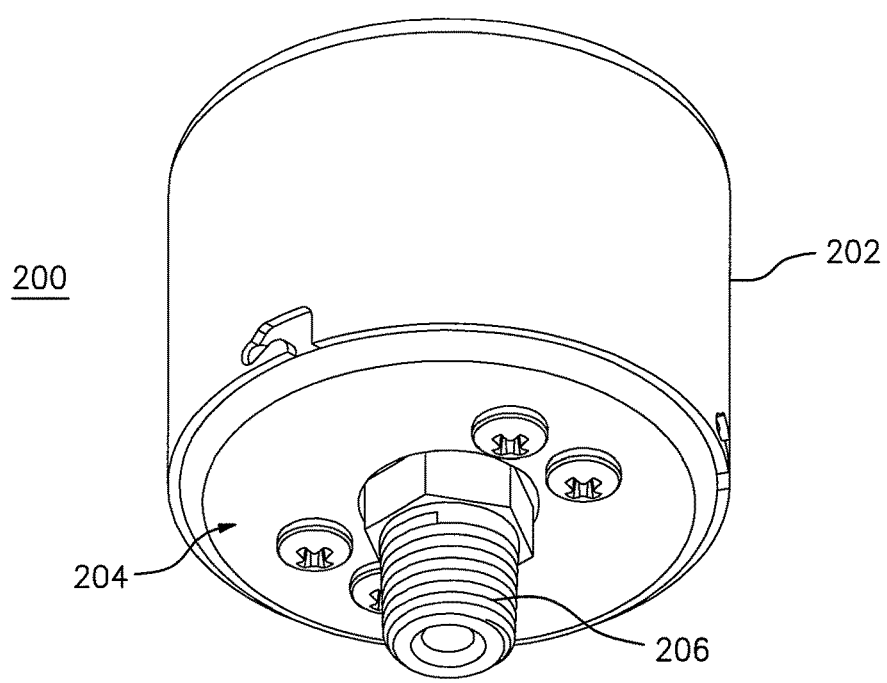
FIG. 4 is a perspective lower view of the housing in FIG. 3
Figure 5:
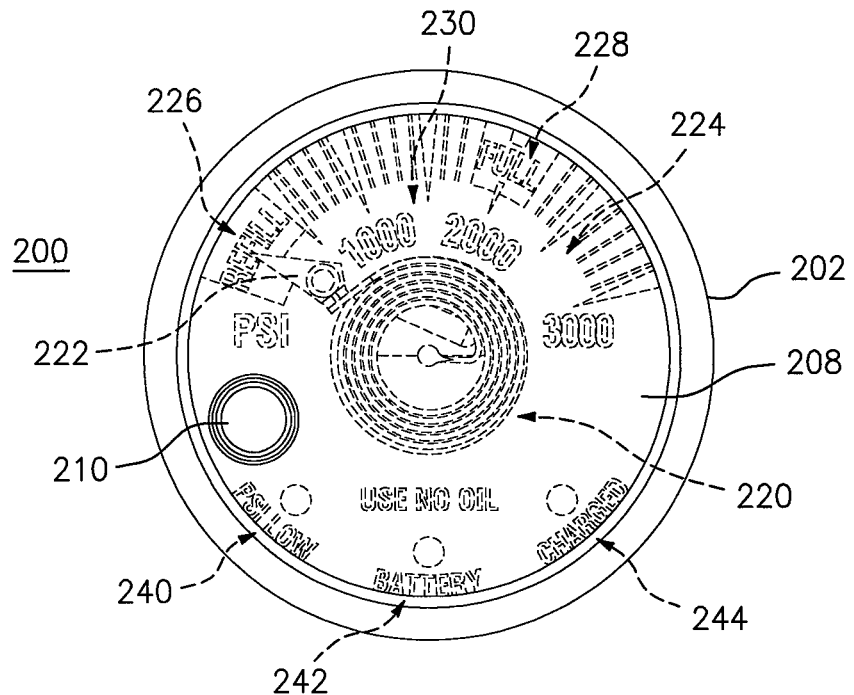
FIG. 5 is a top plan view thereof.
Figure 8:
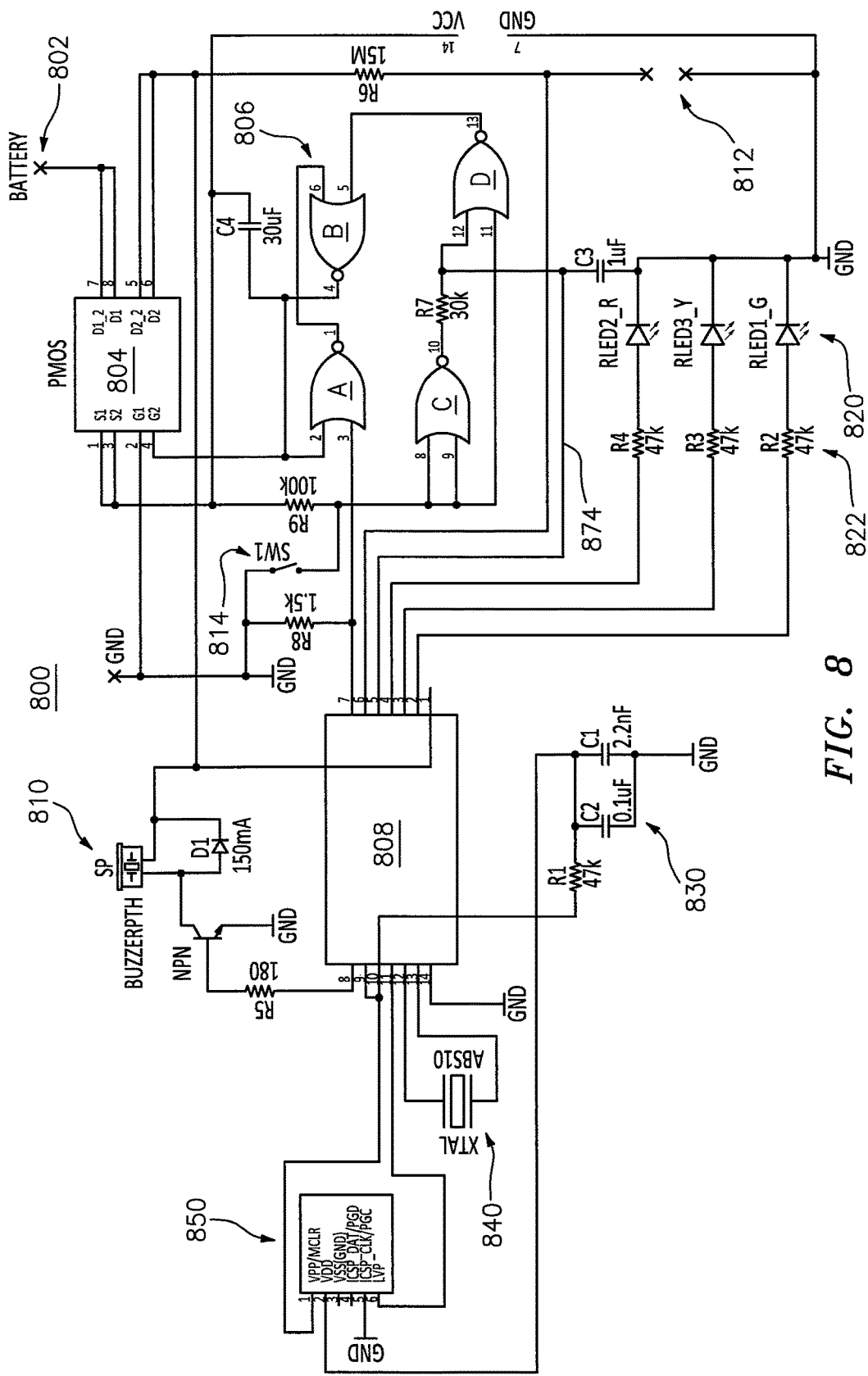
FIG. 8 is a schematic circuit diagram for one implementation of the power management system of FIG. 1.

In certain constructions, pressure monitoring system 100, FIG. 2, with power management system 10' is integrated within a pressure monitoring unit 200, FIGS. 3-5, that correspond to FIGS. 1, 2 and 8 in U.S. Design patent application No. 29/585,168 filed 21 Nov. 2016, which is incorporated herein by reference in its entirety for its design of a PRESSURE GAUGE HOUSING. In this construction, the pressure monitoring unit 200 includes a housing 202 that is mounted to a socket 204 including threaded male connector 206. The housing 200 has a cylindrical shape and, with translucent upper surface 208, acts as a protective cover for mechanical and electronic components of system 200.

A user push-button-type "POWER/SNOOZE" switch 210 extends through the upper surface 208 and is manipulated by a user to initiate one or more of a plurality of functions as described in more detail below. System 200 enables switch 210 to serve as a multiple-functionality switch, assisted by a power on/off flip-flop circuit and a signal transition detection circuit. System 200 includes a Bourdon tube coil 220 having a pointer 222 that is movable relative to indicia 224 including "REFILL"226 and "FULL" 228 in this construction. PSI (Pounds per Square Inch) markings 230 include "1000", "2000" and "3000" in one construction. Color-coding can be provided, such as red for "REFILL" and green for "FULL". Further visually perceptible indicia include "PSI LOW" text and a LED 240, a "BATTERY" text and LED 242, and a "CHARGED" text and LED 244. The position of the pointer 222 of the Bourdon tube coil 220 directly correlates to the pressure within a compressed gas tank or other storage unit. In one construction, upper surface 208 has a diameter of approximately 1 and ⅝ inches, and housing 202 has a height of approximately 1.2 inches. Further details of system 200 are described in more detail below in relation to FIGS. 10-14.

Figure 7B:
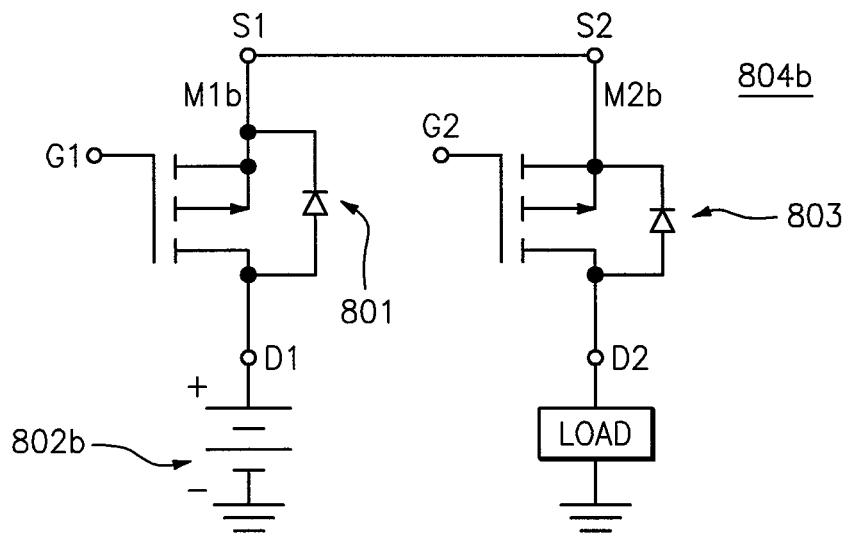
FIG. 7B is an alternative schematic representation of the dual PMOS component of FIG. 7A.
Figure 6:
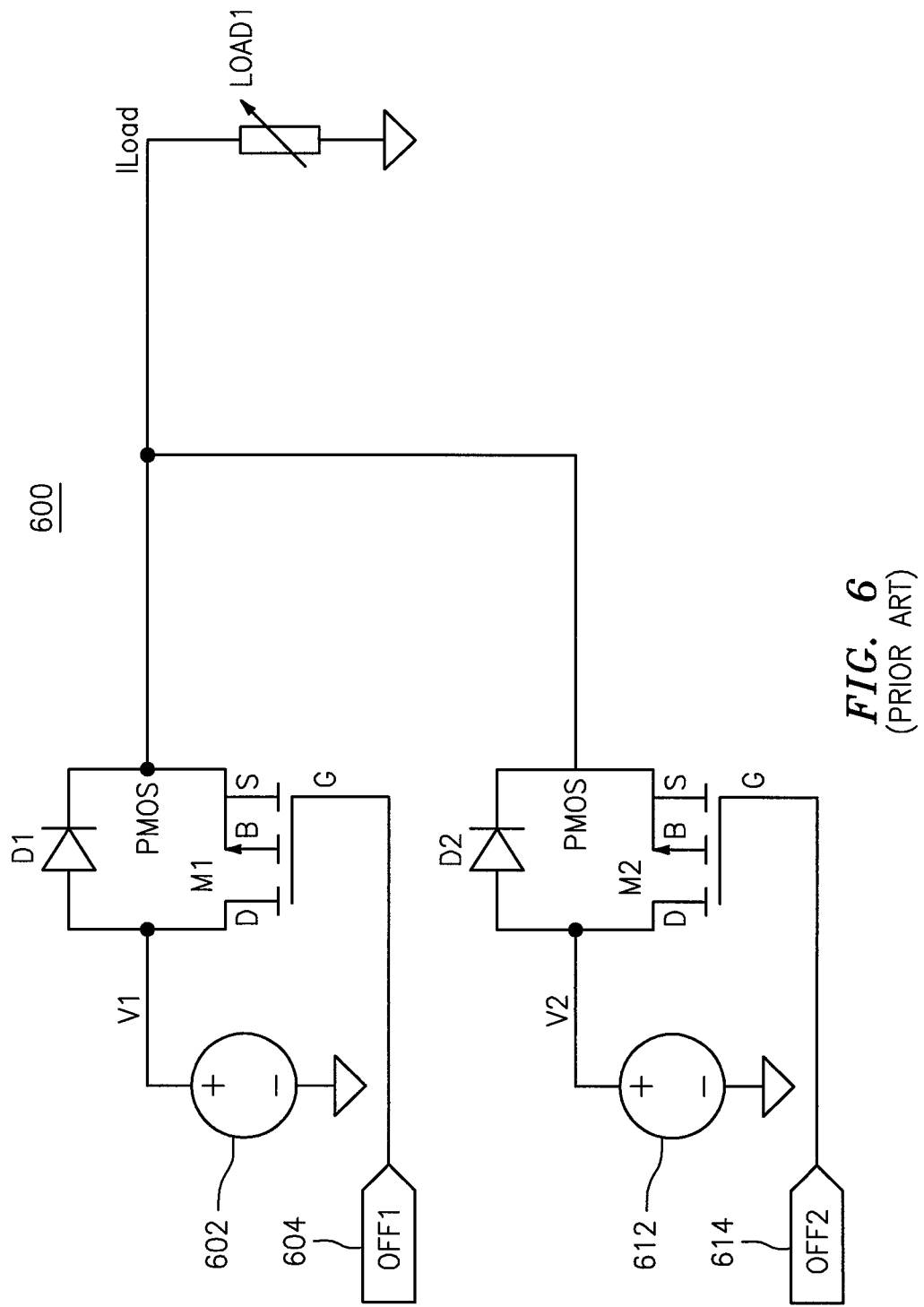
FIG. 6 is a schematic diagram of a conventional electronic power management system utilizing dual PMOS with two different power sources.
Figure 7A:
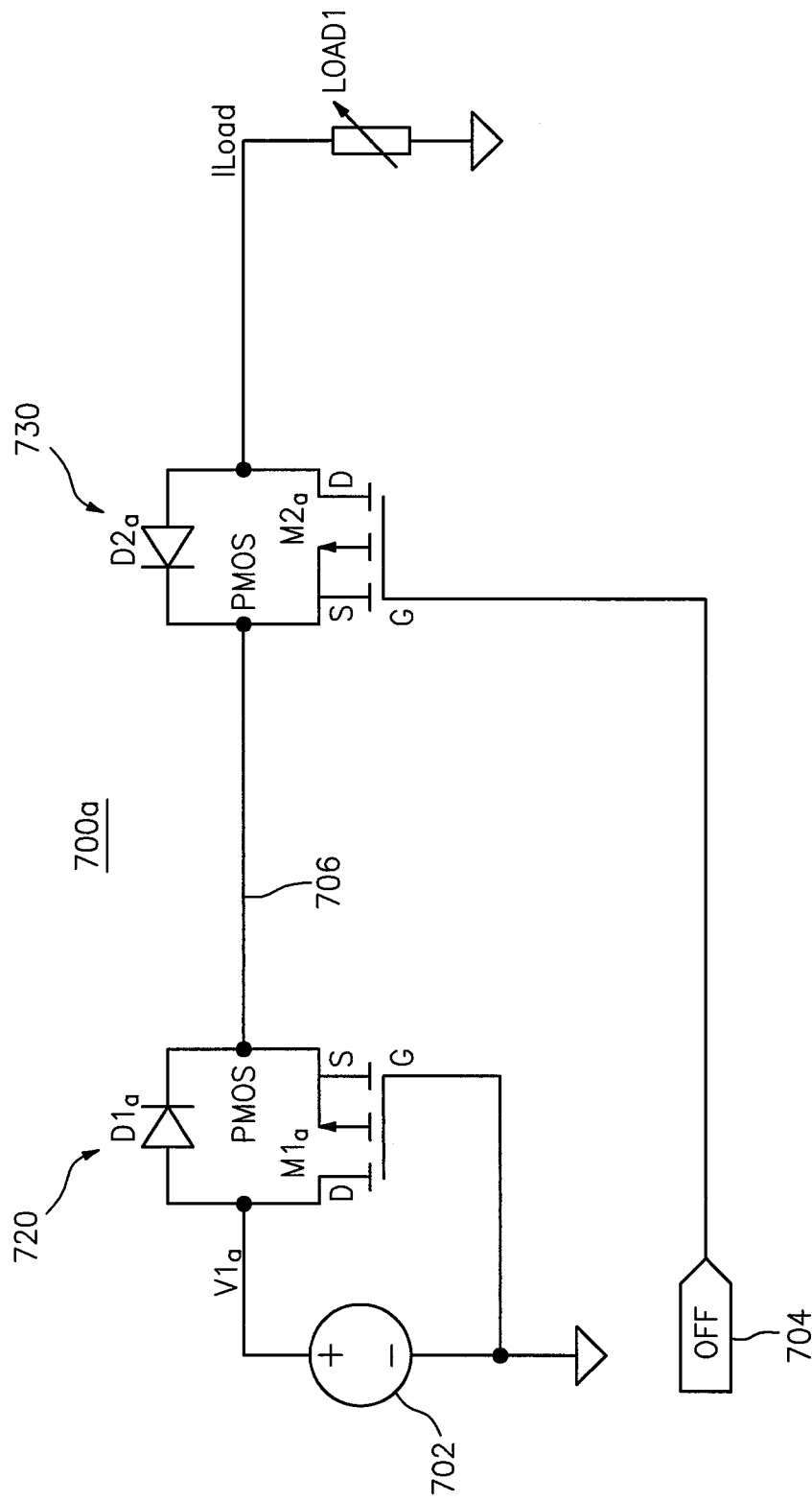
FIG. 7A is a schematic diagram of a power management system according to the present invention utilizing a single power source for a dual PMOS component with PMOS intrinsic diodes shown facing toward each other.

Differences between gate-controlled switching within a conventional power management system relative to gate-controlled switching for power management systems according to the present invention can be appreciated by comparing prior art system 600, FIG. 6, with inventive system 700a, FIG. 7A. Conventional electronic power management system 600, FIG. 6, utilizes PMOS M1 and M2 with two different power sources 602 and 612 which generate voltages V1 and V2, respectively. One or both of power sources 602 and 612 may each be a battery or a wall-plugged transformer supply.

Voltages V1 and V2, FIG. 6, represent two different voltage supplies, and PMOS M1 and M2 embody source reversal protection and on/off control, respectively. Diodes D1 and D2 are the parasitic diodes in M1 and M2, also referred to as intrinsic diodes. The load LOAD1 consumes the power supplied by the circuit. The drain, source and gate PMOS terminals are labelled D, S, and G respectively for each of M1 and M2. The source terminal S is internally connected to the transistor's bulk B, also referred to as the substrate, to configure M1 and M2 as three-terminal devices. The input signals 604 and 614 labelled OFF1 and OFF2, respectively, control the ON/OFF state of PMOS M1 and M2, respectively. A user turns on only one PMOS at a time by setting its control signal low (e.g., by connecting the gate G to ground or zero volts), while all other control signals remain high. The single PMOS that is thus selected to turn on then conducts current Iload to the load. The turned-on PMOS' parasitic diode D1 or D2 is typically slightly forward biased and will also conduct current that contributes to the load current Iload. At the same time, the remaining PMOS devices are turned off, and their parasitic diodes are reverse biased if their associated power source is turned off at zero volts, thus preventing any reverse current from backing up from the load LOAD1 and then flowing from the source to the drain and back through the (possible zero volt) power source to ground.

In case any of the power voltage source V1 or V2, FIG. 6, is accidentally inverted when the control signals OFF1 and OFF2 are high and the PMOS M1 and M2 are turned off, their respective diodes will be reverse biased and therefore no appreciable current will flow through them, thus protecting the load element LOAD1 from a reverse current. Further, any PMOS transistor that is added in parallel to system 600 also incorporates another power source to the system and must be connected with its parasitic diode pointing in the forward direction towards the load, that is, with its parasitic diode biased toward LOAD1.

Power management system 700a according to the present invention, FIG. 7A, utilizes a single power source 702 for a dual PMOS component with PMOS intrinsic diodes D1a and D2a shown facing toward each other, with second diode D2a pointed away from the load LOAD1. The first important difference between conventional system 600 and inventive system 700a is that the circuit is now divided in two functional sections 720 and 730. In the first section 720, PMOS M1a implements reverse voltage protection, while PMOS M2a implements on/off control in the second section 730 as controlled through signal OFF 704. Another important difference is that while the parasitic diode D1a in M1a is pointing in the direction of the system load, the parasitic diode D2a in M2a is pointing in the opposite direction relative to the load LOAD1. This enables the load LOAD1 to be turned off to zero voltage, while the wire node 706 connecting M1a's source S to M2a's source S remains powered on. The node 706 connecting both PMOS sources must remain high because this node powers the necessary circuitry (flip-flop and delay circuits in some constructions, such as described in more detail below) that controls the OFF signal, and it also has source reversal protection.

Notice that if the source S and drain D connections in M2a were reversed, with the parasitic diode D2a now permitting current flow in the direction of the source S towards the load, the circuit 700a would cease to function correctly. Applying a positive voltage at input OFF 704 would still turn M2a off, but the parasitic diode D2a would be forward biased and would continue to drive current to the load. As a result, the voltage across the load would be higher than zero. In other words, it is a realization of the invention that the circuit in FIG. 7A only works as shown, with D2a pointing back to the source S.

Another observation is that the M2a circuit in FIG. 7A seems to contradict the orientation of the M1 circuit diode D1 and the M2 circuit diode D2 in FIG. 6, each of which is biased toward supplying current to the load LOAD1, and therefore we would not expect section 730 to function properly. However, this is not the case. In fact, the orientation shown in FIG. 7A is required to achieve inverse protection and effective on/off control according to the present invention utilizing a single power source.

Dual PMOS component 804b, FIG. 7B, has PMOS M1b and M2b with source terminals S1 and S2 connected in the same configuration as for PMOS M1a and M2a of system 700a, FIG. 7A. The positive terminal of a battery 802b is connectable to drain terminal D1 of PMOS M1b; inversion protection is provided when the other terminal of the battery is connected to gate G1. Source power is provided to a load LOAD connected to drain terminal D2 when gate G1 is connected to ground with the negative terminal of battery 802b and when gate G2 is enabled by an "on" signal (described in more detail below).

Each PMOS device M1b and M2b is a three-terminal device, with terminals named source S1 and S2, gate G1 and G2, and drain D1 and D2, respectively. Each source terminal S1 and S2 is internally connected to the transistor's bulk, also referred to as the substrate. A parasitic internal diode 801, also referred to as an intrinsic diode, is established between the source S1 and the drain D1, and a parasitic internal diode 803 is established between source S2 and drain D2. In one construction, the two PMOS devices are located on a single dual-PMOS integrated circuit package.

In preferred constructions, the directionality in the connection of these two PMOS devices is as follows. The inversion protection PMOS device has its drain terminal connected to the positive terminal of the battery, its gate terminal is connected to ground, and its bulk and source terminal powers the on/off control PMOS device, the flip-flop switch and the transition detection circuit. The on/off control PMOS device has its bulk and source terminal connected to the bulk source terminal of the inversion protection PMOS device, its gate terminal connected to the flip-flop switch output, and its drain terminal powers at least the sensor and the microprocessor.

In preferred constructions, the circuit topology ensures a specific behavior of the parasitic internal diode in each one of the PMOS devices as follows. The parasitic internal diode 801 of the inversion protection PMOS device M1b turns off (that is, creates an open circuit) if the battery polarity is inverted. The parasitic internal diode 803 of the on/off control PMOS device M2b turns off (that is, creates an open circuit) if the flip-flop switch output applies a positive voltage on this PMOS gate terminal that forces the PMOS to turn off, effectively shutting off power at least to the sensor and microprocessor as described in relation to FIG. 8.

One electronic implementation of a power management system 800 according to the present invention is illustrated in FIG. 8 having wire-pads 802 for a battery, dual PMOS component 804, a quad NOR 806 with NOR gate A through NOR gate D, a microprocessor 808 which generates "power off" signal 809, an acoustic sounder such as an alarm buzzer 810, and a reed switch 812 which is normally open until closed by a magnet on pointer 222, FIG. 5, for example. The mechanical reed switch 812 completes a circuit that sends an input to the microprocessor 808 when a low pressure is reached in the compressed gas tank. The microprocessor 808 may be chosen from any of a number of commercially available microprocessors, particularly 16-bit micro-controller commercial products which include a central processing unit (CPU), internal timers with interrupt capability, basic clock, analog to digital conversion capability, a random access memory (RAM), and input/output (I/O) ports with interrupt capability.

Normally open switch 814, FIG. 8, is "momentarily" actuated by a user pressing button 210, FIGS. 3 and 5, for example. In other words, switch 814 is closed only while mechanical pressure is applied by a user. Visible LEDs 820 include red R for LED2, yellow Y for LED3 and green G for LED1 in one construction, with resistors 822 of R4, R3 and R2, respectively. The LEDs 820 are selectively powered by the microprocessor 808 as described in more detail below. The operation of system 800 for certain pressure monitoring applications is described in more detail below in relation to FIGS. 10 and 11.

In this construction, power management system 800 further includes resistor-capacitor combination 830 with resistor R1 and capacitors C1 and C2 which is a requirement of the particular microprocessor/JTAG interface configuration. Component 840 is a crystal to drive the microprocessor internal clock and component 850 is a JTAG (Joint Test Action Group) connector to download the microprocessor software from a host computer in the illustrated construction. Capacitor C4 ensures that the flip flop switch 860, FIG. 9A, will be in the "off" state when the battery power source is first installed. The combination of capacitor C3 and resistor R7, connected at a node 874, behave as a signal delay element in the implementation of the transition detection circuit. The transition detection circuit 870 produces a signal pulse only when the user switch is pressed, but not when it is released, thus avoiding a potential conflict in the operation of the flip/flop switch.

Figure 9A:
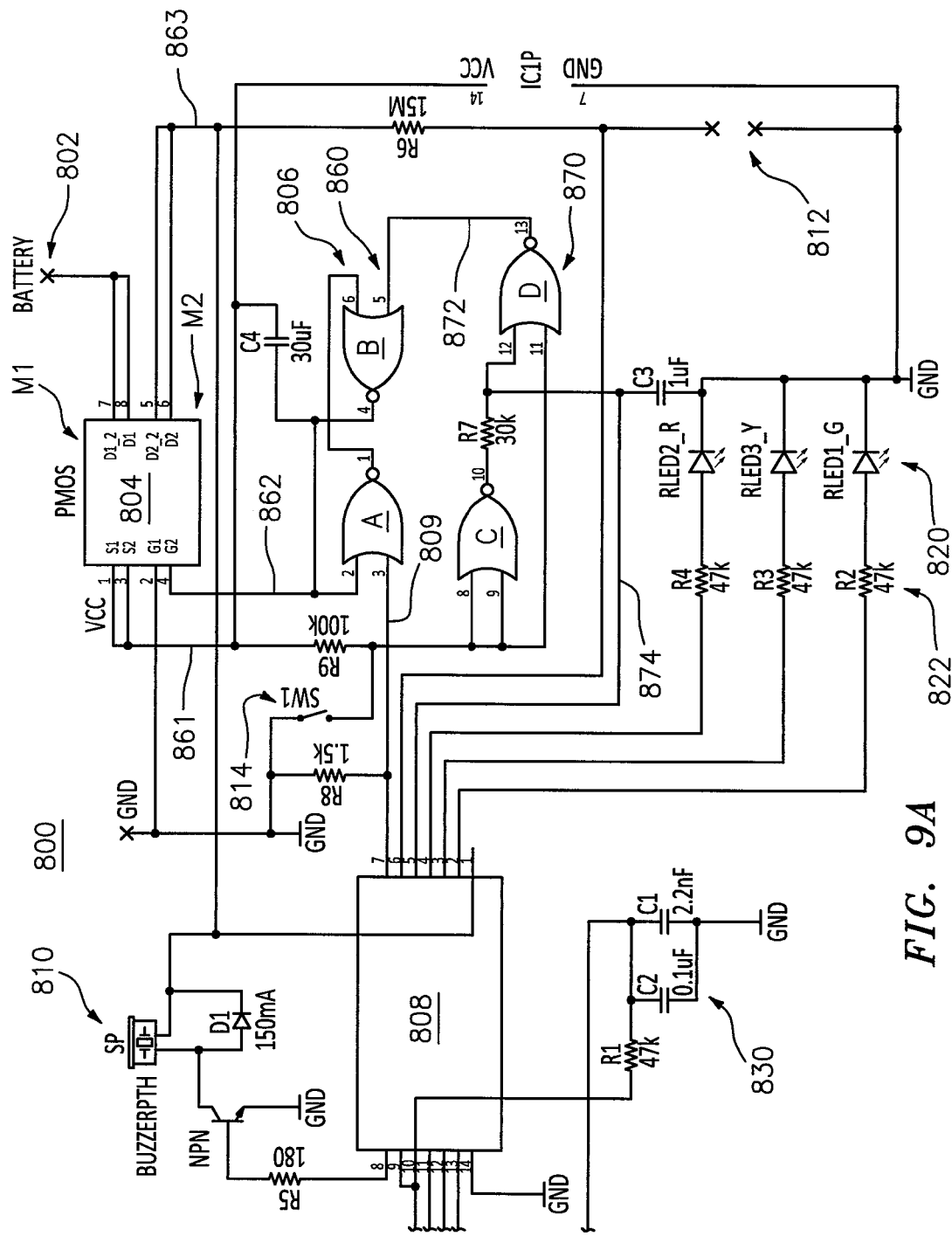
FIG. 9A is an enlarged view of the right-hand side of FIG. 8.

The electrical configuration of dual PMOS component 804, having first and second PMOS M1 and M2 as labelled in FIG. 9A, can be implemented as described above in relation to FIGS. 7A and 7B. One suitable dual p-channel MOSFET is Model Si4931DY currently available from Vishay Siliconix, which has two pins numbered 7 and 8, FIGS. 8 and 9A, for drain terminal D1 and two pins numbered 5 and 6 for drain terminal D2. Source terminals S1 and S2 are connected to pins 1 and 3, respectively, and gate terminals G1 and G2 are connected to pins 2 and 4, respectively. Source terminals S1 and S2 of PMOS M1 and M2 are at a power source voltage Vcc, labelled as 861; voltage Vcc is provided by the battery to drain terminal D1. System power 863 is supplied from drain terminal D2 of PMOS M2 when activated by signal 862 of flip/flop switch 860.

In this construction, NOR gates A and B, FIG. 9A, of the quad NOR component 806 embody a flip/flop switch 860, which includes capacitor C4 for initial condition bias and generates on/off signal 862 that is delivered to source terminal G2 of PMOS M2. NOR gates C and D embody transition detection circuit 870, which also includes resistor R7 and capacitor C3 and generates "power on" signal 872.

Figure 9B:
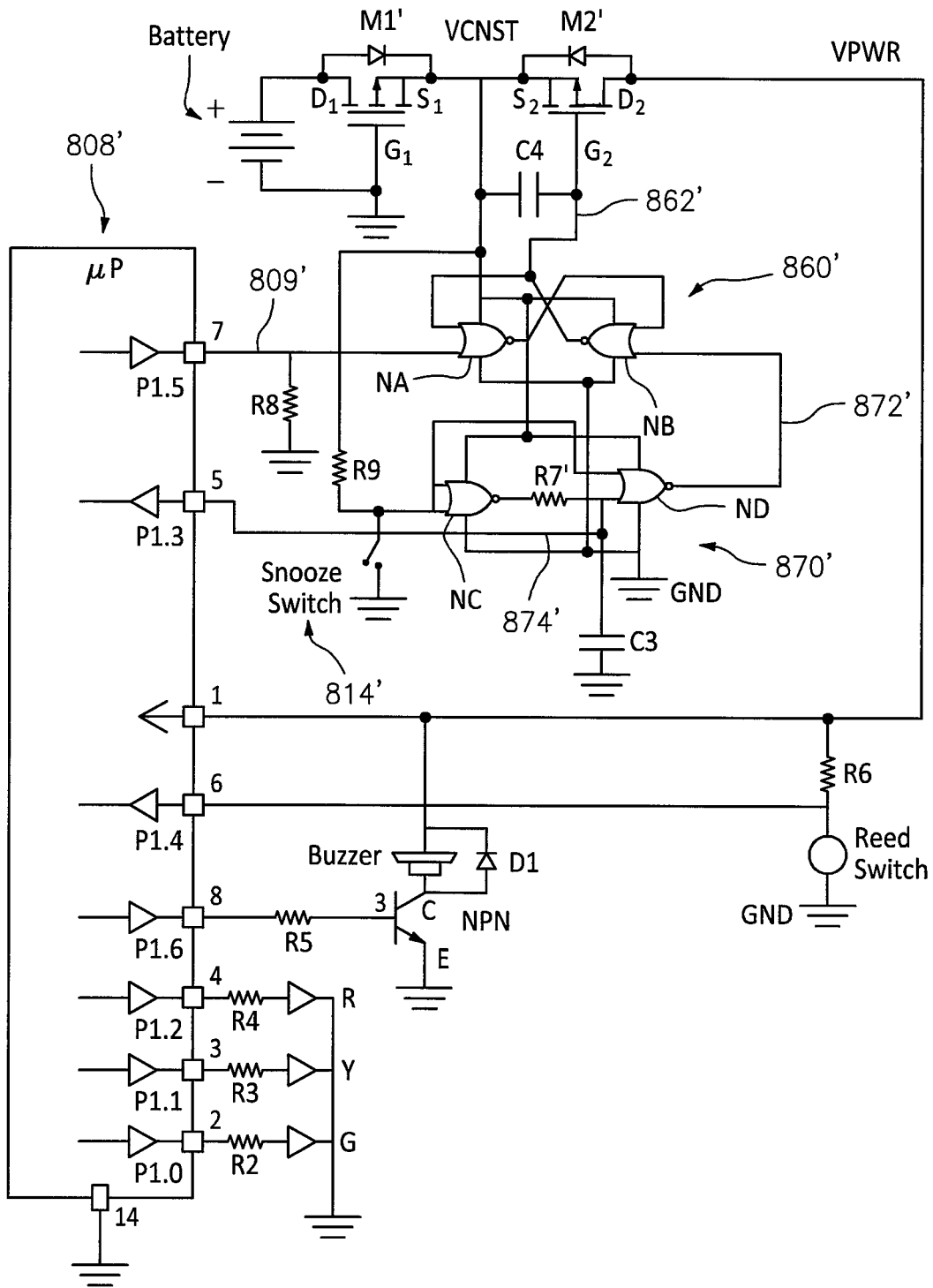
FIG. 9B is a schematic diagram of a circuit that is similar to that depicted in FIGS. 8 and 9A.

An alternative quad NOR arrangement is illustrated in FIG. 9B with NOR gates NA and NB of a flip/flop switch 860', which generates on/off signal 862' that is delivered to an on/off control circuit including PMOS M2'. NOR gates NC and ND with resistor R7' and capacitor C3, connected at a node 874', are part of a transition detection circuit 870' that is responsive to Snooze switch 814' to generate "power on" signal 872' when switch 814' is initially depressed. Microprocessor 808' generates a "power off" signal 809' after detecting that switch 814' has been depressed and held for at least a predetermined period of time.

The node 874' that connects resistor R7 with capacitor C3 is connected to the microprocessor's input P1.3 (pin 5) to monitor the state of the user switch 814' in FIG. 9B for this construction according to the present invention. This node 874' is the logic inversion of the voltage at the user switch 814' generated by NOR gate NC. Connecting this inverted image of the user switch instead of the switch itself ensures that the microprocessor's input pin 5 remains at zero volts when the microprocessor is powered off and the user switch is not pressed. This avoids powering on the microprocessor through its internal electrostatic discharge (ESD) protection circuit at the I/O port, and thus eliminates the potential risk of CMOS latch up and abnormal circuit operation. Similarly, the rest of the overall circuit design ensures proper operation when the microprocessor is powered off. Specifically, output port P1.5 is held low by an external pull-down resistor R8 during the microprocessor power-off state, ensuring that the on/off flip-flop circuit can be swung back to its "on" state by pressing the user switch to turn the power back on. Ground GND is shown at multiple points throughout FIG. 9B.

Figure 10:
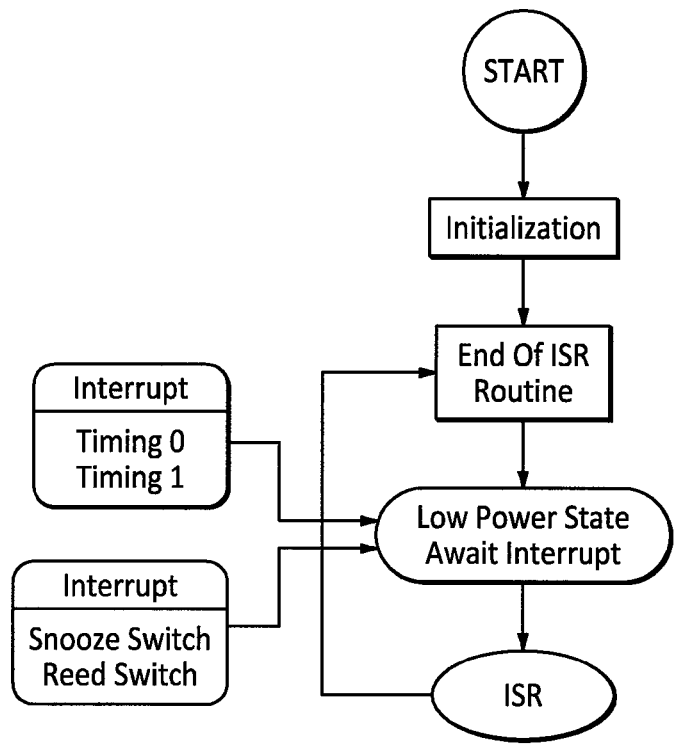
FIG. 10 is a schematic diagram of programmed system operation.

In one construction, the microprocessor 808 is a MSP430F20x2 TI microprocessor and is programmed as follows. FIG. 10 is a schematic diagram 1000 indicating the interrupt-based operation of the software routine for system 800, FIGS. 8 and 9A. The interrupt signals are originated by either timing or input port change events. The details are described in the following sections. A system according to the present invention enables a simple push-button-type switch, such as switch 210, FIG. 2, to serve as a multiple-functionality switch, assisted by a power on/off flip-flop circuit and a signal transition detection circuit to include electronic power-off capability.

After start and initialization, steps 1002 and 1004, FIG. 10, the software program signals the microprocessor to enter a minimum-activity low power state to await timing and port interrupts, steps 1006 and 1008, respectively. When an interrupt occurs, the corresponding interrupt service routine (ISR) 1010 will process the interrupt. When done, the software calls an end of ISR procedure, at the end of which the microprocessor returns to a low power state to await the next interrupt.

Table 1 below lists the various relevant pins on the MPS430F20x2 microprocessor. The port designation numbers are utilized as described below:

TABLE 1

Pin description

| MPS430F20x2 PORT DESIGNATION | PACKAGE PIN NUMBER | FUNCTIONAL NAME | DIRECTION | PULL-UP/PULL-DOWN | DESCRIPTION |
|---|---|---|---|---|---|
| P1.0 | 2 | Green LED | Out | | Active high |
| P1.1 | 3 | Yellow LED | Out | | Active high |
| P1.2 | 4 | Red led | Out | | Active high |
| P1.3 | 5 | Snooze button (inverted logic) | In | | Low: when not depressed. High: pressed. |
| P1.4 | 6 | Reed switch | In | | High: Standby. Low: low pressure. |
| P1.5 | 7 | Power off | Out | External pull-down | High: Power off. Low: Functional. |
| P1.6 | 8 | Sounder | Out | | High: Turn on Low: Turn off |
| P1.7 | 9 | Unused | Out | | |
| | 1 | VDD power | | | |
| | 14 | Ground | | | |

The relevant timing parameters associated with the software timing interrupt services are listed in Table 2 below:

TABLE 2

Clock and main counter parameters

| PARAMETER | VALUE |
|---|---|
| Timer clock frequency | 32,768 Hz. |
| Timer clock period = 1/32,768 Hz | 30.5 μsec |
| Full counter run count = $2^{16} - 1$ | 65,535 |
| Counter full run period = 65,536/32,768 Hz | 2 seconds |

Timer 0 interrupt is responsible for creating the sound vibrations in the acoustic sounder, as well as for determining the sound's pitch. Timer 0 interrupt occurs every timer counter (PIEZOHALF) incremental count of 8 for high acoustic pitch, or every incremental count of 16 for low acoustic pitch.

The associated interrupt service routine (ISR) toggles the acoustic sounder on and off to create an acoustic alarm effect. Therefore, the incremental count of 8 or 16 clock periods represents the acoustic sound half period. The resulting frequencies are presented in Table 3 below:

TABLE 3

Acoustic sounding frequencies

| PARAMETER | VALUE |
|---|---|
| Acoustic frequency (normal) = 1/(16 × 30.5 μsec) | 2 KHz |
| Acoustic frequency (power off) = 1/(32 × 30.5 μsec) | 1 KHz |

Timer 1 interrupt controls the triggering and silencing of the acoustic sounder alarm, and also the LED indications. Timer 1 interrupt occurs in two occasions during every main counter full cycle:

Case 1: Timer 1, Case 1 Interrupt occurs once in the full timer count cycle when the main timer counter reaches a count of 800 for a standby state, or a count of 2,500 for a low pressure state, or a count of 62,000 during power off.

Case 2: Timer 1, Case 2 interrupt also occurs periodically, whenever the main timer counter reaches its full count before rolling over to zero.

In one construction, Case 1 entails the following:

1 Turn all LEDs off.

2 If low pressure state turn off sounder interrupt.

3 Restart the main timer counter every three times going through this step to get a too-too-too-too acoustic effect.

In one construction, Case 2 entails:

1 If standby state and "low battery", turn yellow LED on, with green and red LED off.

2 Else, if low pressure state, turn red LED on, with green and yellow LED off.

3 If low pressure and within snooze period, turn off acoustic sounder interrupt.

The sounder interrupt enable controls the functionality and pitch of the acoustic sounder as detailed in Table 4 below:

TABLE 4

Sounder interrupt enable
Sounder timing interrupt enable

| TURN OFF | TURN ON |
|---|---|
| During timer interrupt case 2 ISR if Reed switch indicates low pressure as long as the snooze counter is greater than zero and has not counted down yet to zero to end snooze time. Result: Turn off sounder after alarm has already alerted low pressure, but snooze button has been pressed to snooze | During timer interrupt case 2 ISR if Reed switch indicates low pressure once the snooze counter times out down to zero signaling the end of snooze time or whenever a snooze count of zero indicates no currently logged snooze request. Result: Turn on sounder to alert for low pressure after snooze time has elapsed, or before any snooze has been requested. During timer interrupt case 2 ISR when it has been detected that the snooze button has long been held down. Result: Turn on sounder to alert that power is going down. |
| During timer interrupt case 1 ISR for low pressure. Result: Modulate too-too-too-too effect. | |
| At the end of every interrupt service routine Result: Modulate too-too-too-too effect. | |

Table 4 above illustrates that the sounder interrupt enable is dependent on the snooze counter. Table 5 below provides for more information on the snooze counter. The snooze counter controls the snooze capability that silences the alarm only for a finite time after being triggered by a low pressure condition:

TABLE 5

Snooze counter

| SNOOZE COUNTER EVENT | TRIGGERED BY |
|---|---|
| Cleared to zero | The end of every interrupt service routine if a low pressure condition has been newly reported. |
| Initialized to a count of 1800 | The end of every interrupt service routine if the snooze button has been newly pressed. |
| Decremented | During timer interrupt case 2 ISR if Reed switch signals low pressure and snooze counter >0. |

The on/off power states for the three LEDs are also controlled by timer 1 interrupt, as illustrated in Table 6 below:

TABLE 6

LED on/off power control

| | RED LED | | GREEN LED | | YELLOW LED | |
|---|---|---|---|---|---|---|
| EVENT | TURN OFF | TURN ON | TURN OFF | TURN ON | TURN OFF | TURN ON |
| At the end of every interrupt service routine | Yes | | Yes | | Yes | |
| Case 1 of Timer 1 interrupt | Yes | | Yes | | Yes | |
| Case 2 of Timer 1 service routine | | Low pressure Snooze button long | Low pressure Snooze button long | Standby | Low pressure Snooze button long | Standby and low battery |

TABLE 6-continued

LED on/off power control

| | RED LED | | GREEN LED | | YELLOW LED | |
|---|---|---|---|---|---|---|
| EVENT | TURN OFF | TURN ON | TURN OFF | TURN ON | TURN OFF | TURN ON |
| | | held Power down | | held Power down | | held Power down |

The "power off" procedure can be implemented as follows. The mechanism to power off the system is to hold the snooze button down long enough. The microprocessor recognizes this condition and eventually generates a power off signal coming out from pin P1.3 to power off the external power on/off flip-flop. The software mechanism for power off uses the timer 1 interrupt and the hold counter. The hold counter is reset to zero every time the snooze button is released, and it is set to a count of 3 every time the snooze button is pressed.

During timer interrupt case 2 ISR, if the snooze button state is detected as pressed, then if the hold counter is greater than zero, it is decremented. Otherwise, if the hold counter is zero, this indicates that the snooze button has been pressed long enough (at least three full timer count cycles), thus calling for power down and causing the following events under program control:

1 Turn off snooze button interrupt enable. Power down is now inexorable.
2 Set timer 1 interrupt comparison count to a high value—62,000.
3 Turn on all LEDs.
4 Signal power down by setting snooze state to snooze power-off.
5 Turn on acoustic sounder interrupt enable.
6 Modify timer 0 interrupt incremental count to 16 for low pitch acoustic sounder alert.

I/O port interrupt-based services can operate as follows. Input ports P1.3 and P1.4 are monitored by the software to generate a port interrupt when the sensed digital high/low input voltage switches from high to low of from low to high. The software habilitates rising and falling transition interrupt enables as needed. P1.3 senses the snooze button state and P1.4 senses the Reed switch as indicated in Table 7 below:

TABLE 7

| Input PORT states | | | |
|---|---|---|---|
| P1.3 | | P1.4 | |
| HIGH | LOW | HIGH | LOW |
| Snooze when pressed | Snooze not pressed | Switch open. Standby. Gauge is pressurized | Switch closed. Low pressure. |

The "power off" procedure can be implemented as follows. The capability to power off the battery-operated system using one single multi-functional switch for snooze and power off is at the center of the electronic innovation of the new oxygen alert design according to the present invention. This design feature relies on an external power on/off flip-flop and an edge detection circuit.

Figure 11:
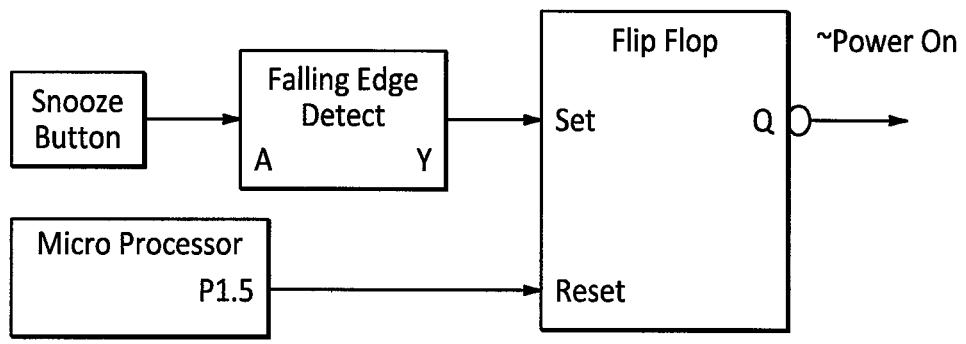
FIG. 11 is a schematic block diagram of components of the "power off" module.

FIG. 11 shows the block components 1100 of the "power off" module. The output signal 1103 of snooze button 1102 is normally high when the button is not pressed, and low when the button is pressed. The falling edge detect circuit 1104 takes in the output signal 1103 of the snooze switch 1102 and generates a signal 1105 with a positive pulse on a falling edge, that is, only when the button snooze 1102 is pressed, and remains low when the button is released. The positive pulse sets the on/off flip-flop 1106 and asserts the ~power on signal low, which ends up powering on the system via signal 1107. If the snooze button 1102 is pressed down and held down long enough (a few seconds), the microprocessor MP senses this condition and eventually drives a high signal as signal 1109 out of pin or port P1.5 of microprocessor MP, thus clearing the flip-flop 1106 and deasserts the ~power on signal high, which ends up powering off the system via signal 1107.

Figure 12:
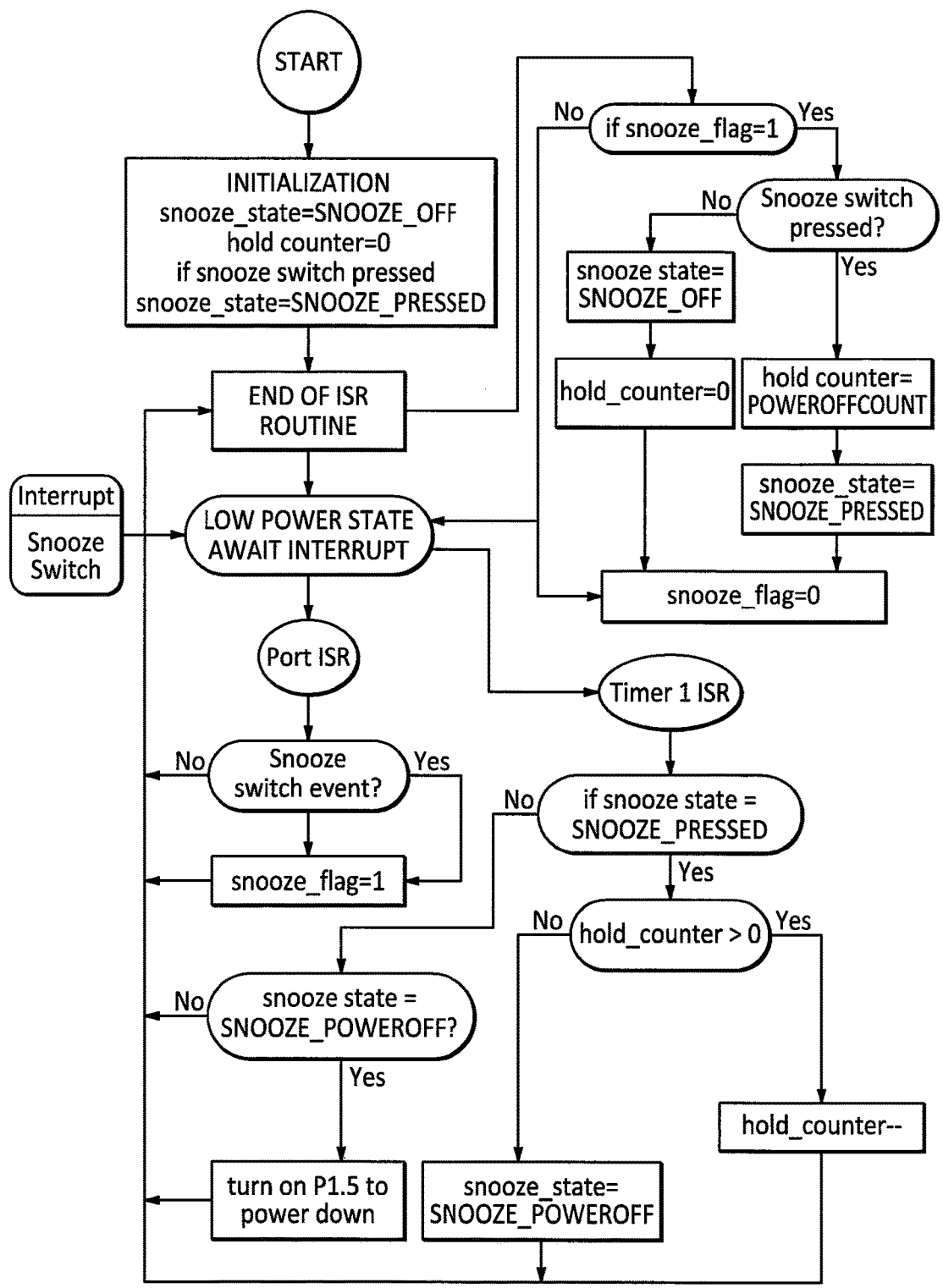
FIG. 12 is a schematic flowchart showing software operation for the "power off" module function.

FIG. 12 is a schematic flowchart 1200 showing software operation for the "power off" module function. The dashed lines of box 1208 illustrate code (software logic) inside of the END OF ISR ROUTINE, step 1206, that instructs LOW POWER STATE AWAIT INTERRUPT, step 1210. The "snooze_flag" variable is set to one in the PORT ISR, step 1214, when a change in the snooze switch (a switch event), step 1212, is detected. The "snooze_flag" variable is examined in the END OF ISR ROUTINE, and if it is found to be 1, the "snooze_state" variable is set to either SNOOZE OFF or SNOOZE PRESSED depending on the pressed or released state of the snooze switch, step 1212. Also, if "snooze_flag" is found to be 1, a "hold_counter" variable is set to a positive value POWEROFFCOUNT if the snooze switch is pressed, or cleared to zero otherwise. Due to timing interrupts, the Timer 1 ISR, step 1216, and the END OF ISR ROUTINE, step 1206, execute repeatedly every two seconds. If the snooze switch is held down, "hold_counter" is then decremented every two seconds, and when the "hold counter" eventually times out to zero and the snooze state is set to SNOOZE_POWEROFF. The next time the Timer 1 interrupt hits the "snooze_state" variable is found to be SNOOZE_POWEROFF. This causes the output P1.5 to be set high, which sets the external on/off flip-flop to power off the system. The microprocessor itself is powered down during system power off and therefore the software does not execute until the system is powered on again.

Figure 13:
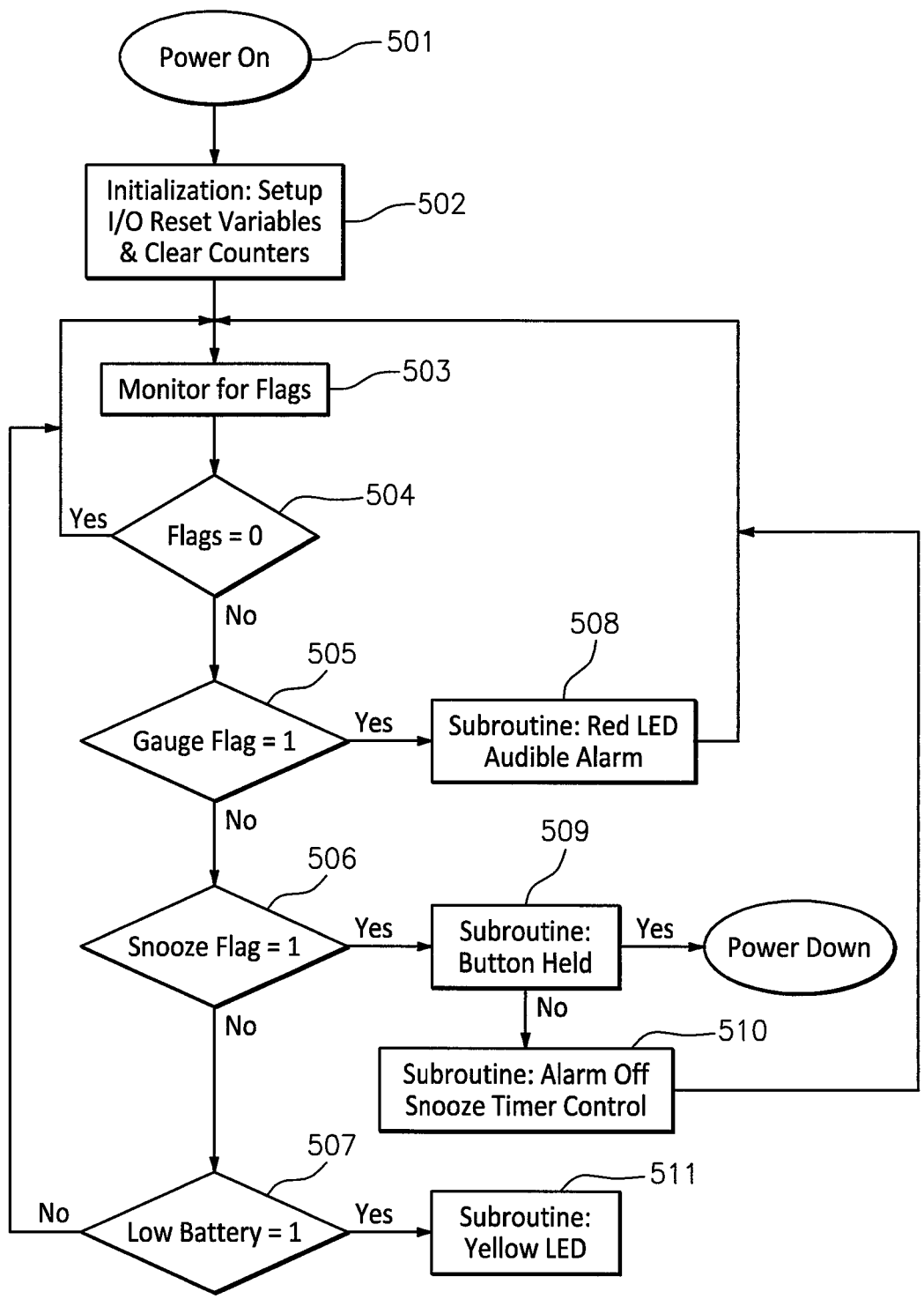
FIG. 13 is a schematic flow diagram of one technique for pressure monitoring according to the present invention as executed by the microprocessor of FIG. 8.

FIG. 13 illustrates a flow diagram of a software module executed by the microprocessor 106 shown in FIG. 2, according to one embodiment of the invention. Similar software modules can be implemented by microprocessor 32, FIG. 1, and microprocessor 808, FIGS. 8-9A, as will be apparent to those of ordinary skill in the relevant arts after reviewing the present disclosure. The module 501, FIG. 13, begins at step 502 by setting up input/outputs (I/O), resetting variables and clearing counters. Next in step 503 input ports are read, which contains the gauge flag information to be checked in steps 505, 506 and 507. If no flags are detected, there is no action required, and the module will run a continuous loop, steps 503 through 507, until a flag is found. Once a gauge flag is detected the program proceeds to step 508 and calls subroutine Red LED, Audible Alarm. Subroutine Red LED, Audible Alarm sends power to the audible alarm as well as to the red LED. The program will return to the continuous loop, steps 503 through 507. Once a snooze flag is detected, step 506, the program proceeds to step 509 and calls subroutine Button Held. Subroutine Button Held uses a counter to determine how long the button is held, a press and release will silence the alarm when there is a gauge flag and a press and hold will send a signal to shut down the system. Once a low battery flag is detected, step 507, the program proceeds to step 511 and calls subroutine Yellow LED. Subroutine Yellow LED sends a signal to power the yellow LED to indicate there is a low battery condition. The program will return to the continuous loop, steps 503 through 507.

Figure 14:
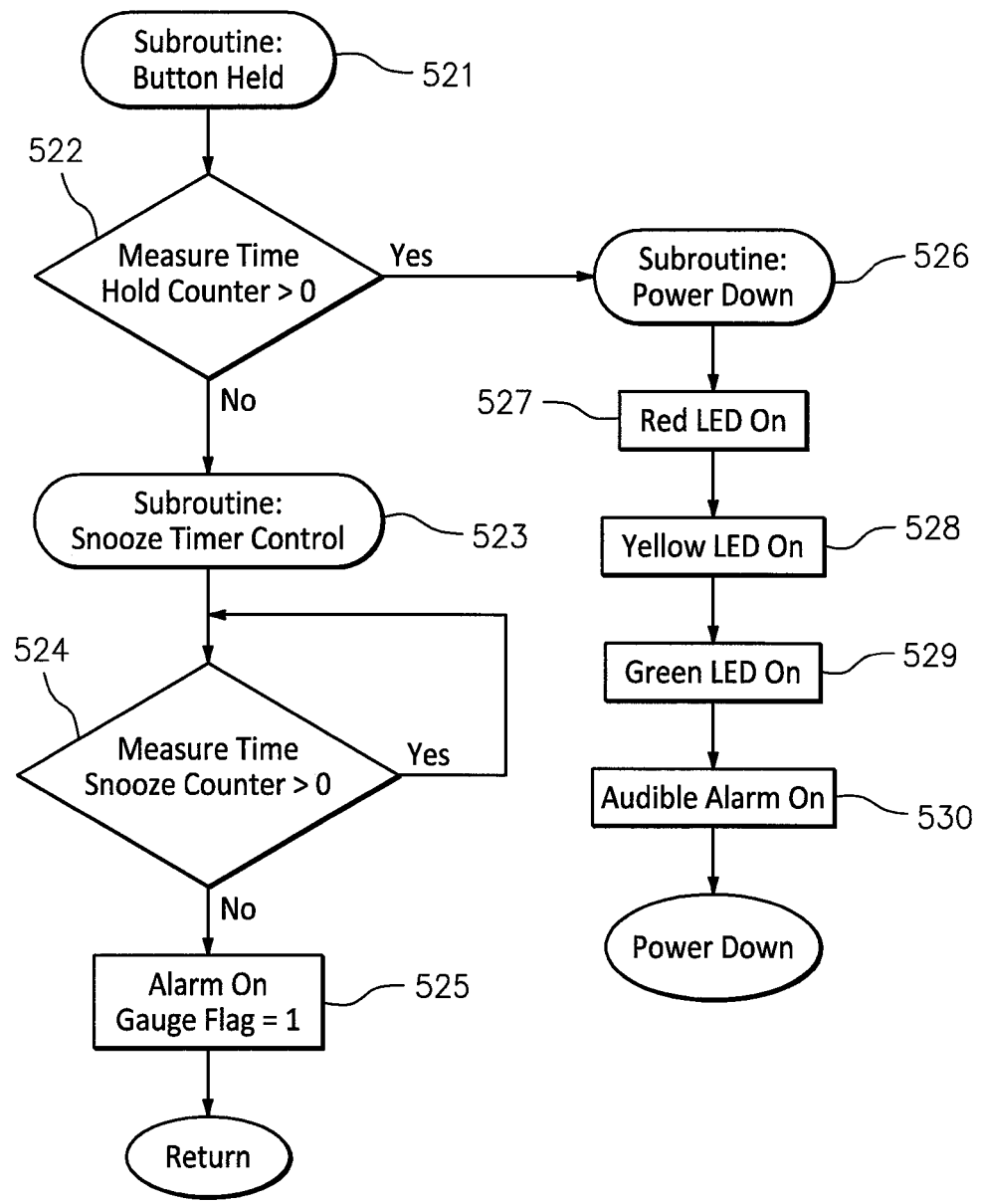
FIG. 14 is a schematic flow diagram of the Button Held subroutine of FIG. 13.

FIG. 14 illustrates a flow chart of the Button Held subroutine called in step 509 of FIG. 13. The determination of a snooze state or shutdown process is implemented in this program. The snooze state is attained when the Hold Counter, step 522, is not met, the button is pushed and released. Subroutine Snooze Timer Control, step 523, is executed. The program will proceed from step 523 to step 524 wherein the Snooze Counter is measured. The program will run a loop between steps 523 and 524 until the parameter is met. Once the count parameter is met the program proceeds to step 525 and then back to the main program at step 503.

In one construction for respiratory oxygen monitoring, after a predetermined period of time (e.g., twenty minutes) after the Snooze function has been initiated, the microprocessor queries the reed switch to determine is pressure is still below the selected threshold (e.g. 500 PSI). The predetermined period of time is selected in this construction based on typical oxygen depletion rates to lower the pressure to approximately 250 PSI. In certain constructions a second Snooze is not permitted, and in other constructions a shorter duration (e.g., five minutes) is timed for the second Snooze request.

The Power Down state is attained when the Hold Counter, step 522, measures a value greater than 0, button is pushed and held. The program proceeds to step 526, subroutine Power Down. Subroutine Power Down runs through step 527, step 528, step 529 and step 530 which in turn has the effect of all LEDs and audible alarm on at the same time until the invention powers down.

Although specific features of the present invention are shown in some drawings and not in others, this is for convenience only, as each feature may be combined with any or all of the other features in accordance with the invention. While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. Further, some computing or software functions conducted by a microprocessor can be implemented with hardware components. It is also to be understood that the drawings are not necessarily drawn to scale, but that they are merely conceptual in nature.

It is the intention, therefore, to be limited only as indicated by the scope of the claims appended hereto. Other embodiments will occur to those skilled in the art and are within the following claims.

What is claimed is:

1. A power management system for use with a single DC power source having inversion protection, the system comprising:
 a normally-open switch that can be activated by a user;
 an on/off circuit including an on/off control gate-controlled switching device for system power, a flip/flop switch having an "on" state and an "off" state to respectively activate and deactivate the on/off control gate-controlled switching device, and a transition detection circuit connected to the normally-open switch;
 a microprocessor; and
 at least one sensor to monitor a condition;
 wherein the microprocessor receives inputs from at least the normally-open switch and the sensor;
 wherein, when connected to the power source with inversion protection, a source voltage is established to power the on/off circuit and the normally-open switch;
 wherein the transition detection circuit (1) generates an "on" signal when the user initially activates the normally-open switch and (2) supplies the "on" signal to the flip/flop switch to change the flip/flop switch to the "on" state to activate the on/off control gate-controlled switching device which, while activated, enables system power from the power source to be provided to at least the sensor and the microprocessor; and
 wherein the microprocessor (1) generates an "off" signal when the normally-open switch is activated for at least a selected period of time and (2) supplies the "off" signal to the flip/flop switch to change it to the "off" state to deactivate the on/off control gate-controlled switching device and thereby disable system power to at least the sensor and the microprocessor.

2. The system of claim 1 further including the inversion protection circuit with a second gate-controlled switching device to accomplish inversion protection.

3. The system of claim 2 wherein the on/off control gate-controlled switching device is a PMOS device and the inversion protection circuit gate-controlled switching device is a second PMOS device that is electrically separate from the on/off control PMOS device.

4. The system of claim 3 wherein each PMOS device is configured as a three-terminal device, each with a source terminal, a drain terminal, and a gate terminal, and each PMOS device includes a parasitic internal diode located between the source and drain terminals of that device.

5. The system of claim 4 wherein the inversion protection PMOS device has its drain terminal connectable to a first terminal of the power source having a first polarity, its gate terminal is connectable to a second terminal of the power source having a second polarity, and its source terminal powers the on/off control PMOS device, the flip-flop switch and the transition detection circuit.

6. The system of claim 5 wherein the on/off control PMOS device has its source terminal connected to the source terminal of the inversion protection PMOS device, its gate terminal connected to the flip-flop switch output, and its drain terminal powers at least the sensor and the microprocessor.

7. The system of claim 6 wherein the parasitic internal diode of the inversion protection PMOS device creates an open circuit if the battery polarity is inverted.

8. The system of claim 7 wherein the parasitic internal diode of the on/off control PMOS device creates an open circuit if the flip-flop switch output applies a positive voltage on the gate terminal of the on/off control PMOS device that forces the on/off control PMOS to turn off, effectively shutting off power at least to the sensor and microprocessor.

9. The system of claim 6 wherein the parasitic internal diode of the on/off control PMOS is biased toward its source terminal.

10. The system of claim 3 wherein the inversion protection PMOS device and the on/off control PMOS device are formed on a single integrated circuit package as electrically separate devices.

11. The system of claim 2 wherein the flip/flop switch and the transition detection circuit utilize different portions of a quad-NOR device.

12. The system of claim 2 wherein the normally-open switch includes a push-button switch that, when pressed, sends a switch signal to the transition detection circuit and the microprocessor.

13. The system of claim 2 further including a user notification device that is activated by the microprocessor to inform the user when the sensor detects a change in the condition being monitored.

14. The system of claim 13 wherein the sensor includes a magnetically-actuated reed switch that, when actuated, indicates the change in the condition being monitored.

15. A power management system having a single DC power source, the system comprising:
 a single DC power source;
 an inversion protection circuit including an inversion protection PMOS device;
 a normally-open switch that can be activated by a user;
 an on/off circuit including an on/off control PMOS device for system power, a flip/flop switch having an "on" state and an "off" state to respectively activate and deactivate the on/off control PMOS device, and a transition detection circuit connected to the normally-open switch;
 a microprocessor;
 at least one sensor to monitor a condition; and
 a user notification device that is activated by the microprocessor to inform the user when the sensor detects a change in the condition being monitored;
 wherein the microprocessor receives inputs from at least the normally-open switch and the sensor;
 wherein a positive source voltage is established by the DC power source and the inversion protection PMOS device to power the on/off circuit and the normally-open switch;
 wherein the transition detection circuit (1) generates an "on" signal when the user initially activates the normally-open switch and (2) supplies the "on" signal to the flip/flop switch to change the flip/flop switch to the "on" state to activate the on/off control PMOS device which, while activated, enables system power from the power source to be provided to at least the sensor and the microprocessor; and
 wherein the microprocessor (1) generates an "off" signal when the normally-open switch is activated for at least a selected period of time and (2) supplies the "off" signal to the flip/flop switch to change it to the "off" state to deactivate the on/off control PMOS device and thereby disable system power to at least the sensor and the microprocessor.

16. A circuit utilizing a single power source to provide inversion protection and power management to a load, the circuit comprising first and second gate-controlled switching devices, each switching device having a source terminal, a drain terminal and a gate terminal, with a parasitic internal diode located between the source and drain terminals and having a cathode connected to the source terminal and an anode connected to the drain terminal, the first switching device having its drain terminal connectable to a first terminal of the power source having a first polarity, its gate terminal is connectable to a second terminal of the power source having a second polarity to provide inversion protection, and its source terminal powers at least the second switching device, and the second switching device has its source terminal connected to the source terminal of the first switching device, its gate terminal connected to a control switch to provide on/off control, and its drain terminal powers the load, and wherein the parasitic internal diode of the second switching device has its cathode connected to its source terminal and therefore is connected to only conduct toward the power source.

17. A method for managing power from a single DC power source having inversion protection, the method comprising:
selecting a normally-open switch that can be activated by a user;
selecting an on/off circuit including an on/off control gate-controlled switching device for system power, a flip/flop switch having an "on" state and an "off" state to respectively activate and deactivate the on/off control gate-controlled switching device, and a transition detection circuit connected to the normally-open switch;
selecting a microprocessor and at least one sensor to monitor a condition;
establishing a source voltage from the power source with inversion protection to power the on/off circuit and the normally-open switch;
utilizing the transition detection circuit (1) to generate an "on" signal when the user initially activates the normally-open switch and (2) to supply the "on" signal to the flip/flop switch to change the flip/flop switch to the "on" state to activate the on/off control gate-controlled switching device which, while activated, enables system power from the power source to be provided to at least the sensor and the microprocessor; and
utilizing the microprocessor (1) to generate an "off" signal when the normally-open switch is activated for at least a selected period of time and (2) to supply the "off" signal to the flip/flop switch to change it to the "off" state to deactivate the on/off control gate-controlled switching device and thereby disable system power to at least the sensor and the microprocessor.

18. The method of claim 17 wherein the on/off control gate-controlled switching device is a P-channel enhancement FET device and the inversion protection circuit gate-controlled switching device is a second P-channel enhancement FET device that is electrically separate from the on/off control P-channel enhancement FET device.

19. The method of claim 17 wherein the on/off control gate-controlled switching device is a PMOS device and the inversion protection circuit gate-controlled switching device is a second PMOS device that is electrically separate from the on/off control PMOS device.

20. The method of claim 19 wherein each PMOS device is configured as a three-terminal device, each with a source terminal, a drain terminal, and a gate terminal, and each PMOS device includes a parasitic internal diode located between the source and drain terminals of that device.

21. The method of claim 20 wherein the inversion protection PMOS device has its drain terminal connectable to a first terminal of the power source having a first polarity, its gate terminal is connectable to a second terminal of the power source having a second polarity, and its source terminal powers the on/off control PMOS device, the flip-flop switch and the transition detection circuit.

22. The method of claim 21 wherein the on/off control PMOS device has its source terminal connected to the source terminal of the inversion protection PMOS device, its gate terminal connected to the flip-flop switch output, and its drain terminal powers at least the sensor and the microprocessor.

23. The method of claim 22 wherein the parasitic internal diode of the inversion protection PMOS device creates an open circuit if the battery polarity is inverted, and the parasitic internal diode of the on/off control PMOS device creates an open circuit if the flip-flop switch output applies a positive voltage on the gate terminal of the on/off control PMOS device that forces the on/off control PMOS to turn off, effectively shutting off power at least to the sensor and microprocessor.

24. The method of claim 17 wherein power is managed in a pressure gauge monitoring system including a spiral Bourdon element, a socket, a housing, a dial, a main PCB with mechanical on/off push button switch as the normally-open switch to silence an alarm.

25. The method of claim 24 further including LED indicators for a low pressure state, low battery state and acceptable operating pressure.

* * * * *